(12) United States Patent
Kasahara

(10) Patent No.: US 12,025,755 B2
(45) Date of Patent: Jul. 2, 2024

(54) TESTING APPARATUS, TESTING METHOD, AND PHANTOM

(71) Applicant: Hitachi, Ltd., Tokyo (JP)

(72) Inventor: Eiji Kasahara, Tokyo (JP)

(73) Assignee: FUJIFILM HEALTHCARE CORPORATION, Chiba (JP)

( * ) Notice: Subject to any disclaimer, the term of this patent is extended or adjusted under 35 U.S.C. 154(b) by 343 days.

(21) Appl. No.: 17/197,451

(22) Filed: Mar. 10, 2021

(65) Prior Publication Data
US 2021/0382155 A1    Dec. 9, 2021

(30) Foreign Application Priority Data
Jun. 3, 2020   (JP) .................................. 2020-096557

(51) Int. Cl.
*G01S 7/52*    (2006.01)
*A61B 8/00*    (2006.01)
*G01S 15/89*    (2006.01)

(52) U.S. Cl.
CPC ............ *G01S 7/5205* (2013.01); *A61B 8/587* (2013.01); *G01S 15/8915* (2013.01); *A61B 8/4461* (2013.01)

(58) Field of Classification Search
None
See application file for complete search history.

(56) References Cited

U.S. PATENT DOCUMENTS

| | | | | |
|---|---|---|---|---|
| 4,331,021 A * | 5/1982 | Lopez | ................ | G01S 7/52052 73/1.86 |
| 4,644,510 A * | 2/1987 | Fujii | .................. | G01S 7/52004 367/87 |
| 4,993,416 A * | 2/1991 | Ophir | ................... | G10K 11/352 600/445 |
| 5,524,636 A * | 6/1996 | Sarvazyan | ............. | A61B 5/064 73/818 |
| 9,265,484 B2 * | 2/2016 | Brewer | .................. | A61B 8/467 |
| 2005/0136002 A1 * | 6/2005 | Fossheim | ................ | A61B 5/01 424/9.4 |

(Continued)

FOREIGN PATENT DOCUMENTS

| | | |
|---|---|---|
| CN | 111050660 A | 4/2020 |
| JP | 2006-166956 A | 6/2006 |

OTHER PUBLICATIONS

Chinese Office Action received in corresponding Chinese Application No. 202110397985.6 dated Jun. 29, 2023.
(Continued)

*Primary Examiner* — Isam A Alsomiri
*Assistant Examiner* — Jonathan D Armstrong
(74) *Attorney, Agent, or Firm* — MATTINGLY & MALUR, PC

(57) ABSTRACT

A testing apparatus has a phantom and a scanning mechanism. The scanning mechanism moves an ultrasonic probe in a scanning direction (x direction) while maintaining a contact state of the ultrasonic probe with the phantom. The phantom includes a heart simulated element simulating a heart which is a tissue of interest, and a simulated element simulating a tissue which is present at a periphery of the heart. A form of the heart simulated element changes continuously in the scanning direction. A change of a form thereof represents a change with respect to time of the heart.

1 Claim, 9 Drawing Sheets

(56) References Cited

U.S. PATENT DOCUMENTS

| | | | |
|---|---|---|---|
| 2005/0240126 A1* | 10/2005 | Foley | A61B 8/06 601/2 |
| 2008/0139933 A1* | 6/2008 | Jeong | A61B 8/587 600/437 |
| 2008/0183075 A1* | 7/2008 | Govari | A61B 8/587 600/437 |
| 2017/0122915 A1* | 5/2017 | Vogt | A61B 8/00 |

OTHER PUBLICATIONS

Chinese Office Action received in corresponding Chinese Application No. 202110397985.6 dated Dec. 5, 2023.

\* cited by examiner

TESTING APPARATUS, TESTING METHOD, AND PHANTOM

CROSS REFERENCE TO RELATED APPLICATION

This application claims priority to Japanese Patent Application No. 2020-096557 filed on Jun. 3, 2020, which is incorporated herein by reference in its entirety including the specification, claims, drawings, and abstract.

TECHNICAL FIELD

The present disclosure relates to a testing apparatus, a testing method, and a phantom, and in particular to a phantom which is used in a test of an ultrasound diagnostic apparatus.

BACKGROUND

Ultrasound diagnostic apparatus have various measurement functions. During a pre-shipping inspection or maintenance of an ultrasound diagnostic apparatus, in order to inspect or confirm that the measurement functions or important measurement functions are functioning normally, a test of the ultrasound diagnostic apparatus is performed.

In the test of the ultrasound diagnostic apparatus, a phantom is used as necessary. A phantom is a construction which artificially simulates an inside of a living body. The phantom generally includes a simulated element which simulates a tissue of interest. The measurement functions of the ultrasound diagnostic apparatus include a measurement function targeted to a heart. In the test of this measurement function, ideally, a phantom including a simulated element simulating the heart is used. However, it is not easy to manufacture a simulated element having a dynamically changing form. In particular, because a heart of a fetus moves rapidly, manufacturing a simulated element simulating the heart of the fetus is not easy.

In manufacturing the simulated element simulating the heart of the fetus, for example, a configuration may be considered in which a pump is connected to a small balloon, and an amount of liquid in the balloon is periodically increased or decreased by control of the pump. However, in this case, a complex mechanism is required, and bubbles tend to easily occur in the balloon.

When a phantom cannot be used, a configuration may be considered in which data acquired in the past are supplied to the measurement function in the ultrasound diagnostic apparatus, and an operation of the measurement function is tested with such data. However, in this case, it is not possible to test the operation of the ultrasound diagnostic apparatus as a whole under the same circumstances as the actual circumstances during an ultrasonic inspection.

JP 2006-166956 A discloses a phantom for an ultrasound diagnostic apparatus. The phantom has, at an inside thereof, a tubular member simulating an artery. A relative positional relationship between the phantom and an ultrasonic probe is fixed.

An advantage of the present disclosure lies in realization of a novel method for simulating a moving tissue. Alternatively, an advantage of the present disclosure lies in realization of a phantom having a stationary simulated element simulating a moving tissue. Further alternatively, an advantage of the present disclosure lies in testing of an ultrasound diagnostic apparatus using such a phantom.

SUMMARY

According to one aspect of the present disclosure, there is provided a testing apparatus comprising: a phantom that includes a tissue-of-interest simulated element which simulates a change with respect to time of a tissue of interest as a change of a form in a scanning direction; and a scanning mechanism that relatively moves an ultrasonic probe with respect to the phantom in the scanning direction.

According to another aspect of the present disclosure, there is provided a method of testing, the method comprising: relatively moving an ultrasonic probe, which executes transmission and reception of ultrasound, with respect to a phantom which includes a tissue-of-interest simulated element which simulates a change with respect to time of a tissue of interest as a change of a form; performing a measurement based on a data array acquired by the relative movement of the ultrasonic probe; and evaluating a result of the measurement.

According to another aspect of the present disclosure, there is provided a phantom comprising; a tissue-of-interest simulated element that simulates a change with respect to time of a tissue of interest as a change of a form in a scanning direction; and a peripheral-tissue simulated element that simulates a peripheral tissue which is present at a periphery of the tissue of interest.

BRIEF DESCRIPTION OF DRAWINGS

Embodiment(s) of the present disclosure will be described based on the following figures, wherein.

DESCRIPTION OF EMBODIMENTS

Figure 1:
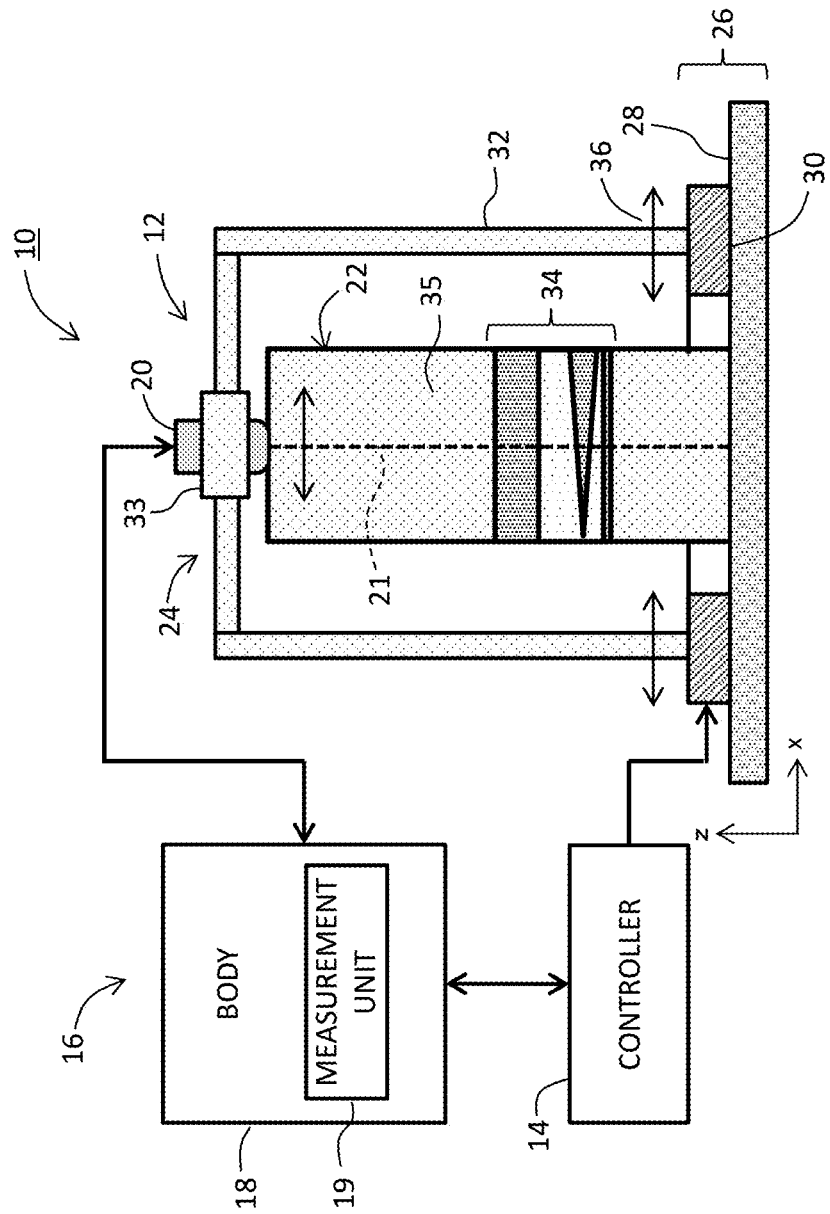
FIG. 1 is a conceptual diagram showing a testing apparatus according to an embodiment of the present disclosure.

An embodiment of the present disclosure will now be described with reference to the drawings.

(1) Overview of Embodiment

A testing apparatus according to an embodiment of the present disclosure comprises a phantom and a scanning mechanism. The phantom includes a tissue-of-interest simulated element which simulates a change with respect to time of a tissue of interest as a change of a form in a scanning direction. The scanning mechanism is a mechanism which relatively moves an ultrasonic probe with respect to the phantom in the scanning direction.

The scanning direction in the phantom (that is, a specific spatial axis) corresponds to a time axis, and the form of the tissue-of-interest simulated element changes continuously or stepwise in the scanning direction. When an ultrasonic probe is relatively moved with respect to the phantom in the scanning direction, a data array can be acquired, which is similar to a data array which is acquired when a change with respect to time of the tissue of interest is observed by an ultrasonic probe in a static state. Because the tissue-of-interest simulated element is a stationary simulated element, manufacture of the simulated element is relatively easy. When the size of the tissue-of-interest simulated element is changed with time, bubbles tend to easily occur, but with the above-described configuration, such a problem can be avoided.

The tissue of interest is a moving tissue, and is, for example, a periodically moving tissue such as the heart. In the embodiment, a heart of a fetus is set as the tissue of interest. The concept of relative movement includes a continuous movement and a step movement. The step movement is a movement in which moving and stopping are repeated. The concept of the change of the form may include, in addition to a change of an external form, a change of an internal form; that is, a change of a structure. With the ultrasonic probe, a two-dimensional data capturing space is repeatedly formed, or a three-dimensional data capturing space is repeatedly formed. The phantom may be fixed and the ultrasonic probe may be moved, or the ultrasonic probe may be fixed and the phantom may be moved.

In an embodiment of the present disclosure, the scanning mechanism causes the ultrasonic probe to relatively and repeatedly reciprocate with respect to the phantom. With the reciprocating motion, a data array for the tissue of interest which moves periodically may be acquired. In an embodiment of the present disclosure, the scanning mechanism causes the ultrasonic probe to relatively and repeatedly reciprocate with respect to the phantom according to a designated period. The period is set manually or automatically.

In an embodiment of the present disclosure, a form of the tissue-of-interest simulated element changes continuously in the scanning direction, and the scanning mechanism relatively and continuously moves the ultrasonic probe with respect to the phantom.

In an embodiment of the present disclosure, the phantom includes a peripheral-tissue simulated element which simulates a peripheral tissue which is present at a periphery of the tissue of interest. A form of the peripheral-tissue simulated element is uniform in the scanning direction. For example, the tissue of interest is the heart of the fetus, and the peripheral tissue having a form uniform in the scanning direction is an amniotic fluid in a mother.

In an embodiment of the present disclosure, the tissue-of-interest simulated element has a line-form element provided in such a manner that a position of existence thereof in a plane orthogonal to the scanning direction changes continuously in the scanning direction. According to such a configuration, the test can be precisely performed using the line-form element. In an embodiment of the present disclosure, the line-form element functions as a strong reflective element, and is used as a tracking target.

In an embodiment of the present disclosure, the scanning mechanism has a holding mechanism which detachably holds the ultrasonic probe, such that a beam scanning plane formed by the ultrasonic probe is orthogonal to the scanning direction.

In an embodiment of the present disclosure, the tissue-of-interest simulated element has a plurality of simulated parts corresponding to a plurality of time phases provided discretely in the scanning direction. The scanning mechanism causes a relative step movement of the ultrasonic probe with respect to the phantom. The plurality of simulated parts may be connected to each other, or the plurality of simulated parts may be placed discretely. Each simulated part may be a three-dimensional simulated part.

In an embodiment of the present disclosure, the scanning mechanism causes the relative step movement of the ultrasonic probe according to a synchronization signal which is output from an ultrasound diagnostic apparatus. For example, the step movement of the ultrasonic probe is executed utilizing a blank period according to a frame rate or a blank period according to a volume rate.

A method of testing in an embodiment of the present disclosure comprises a first step, a second step, and a third step. In the first step, an ultrasonic probe, which executes transmission and reception of ultrasound, is relatively moved with respect to a phantom which includes a tissue-of-interest simulated element which simulates a change with respect to time of a tissue of interest as a change of a form. In the second step, a measurement is performed based on a data array acquired by the relative movement of the ultrasonic probe. In the third step, a result of the measurement is evaluated. All or a part of the three steps may be performed by a user, or may be automated.

A phantom in an embodiment of the present disclosure comprises a tissue-of-interest simulated element, and a peripheral-tissue simulated element. The tissue-of-interest simulated element simulates a change with respect to time of a tissue of interest as a change of a form in a scanning direction. The peripheral-tissue simulated element simulates a peripheral tissue which is present at a periphery of the tissue of interest.

(2) Details of Embodiment

FIG. 1 shows a testing apparatus according to an embodiment of the present disclosure. A testing apparatus 10 illustrated in FIG. 1 is used when a measurement function of an ultrasound diagnostic apparatus 16 is tested. Alternatively, the testing apparatus 10 may be used in other usages.

The ultrasound diagnostic apparatus 16 comprises an ultrasound diagnostic apparatus body (hereinafter simply referred to as a "body") 18, and an ultrasonic probe (hereinafter simply referred to as a "probe") 20 connected to the body 18. The body 18 comprises a transmission circuit, a reception circuit, an image former, a display processor, a display, an inputter, a control unit, and the like. The control unit controls operations of the constituent elements in the body 18, and also executes various measurements. The control unit includes a processor (for example, a CPU) which executes a program. In FIG. 1, a measurement function of the control unit is shown as a measurement unit 19. In the present embodiment, the measurement unit 19 has a function to measure a heart of a fetus in a mother. For example, with the measurement unit, a change with respect to time of a position, a change with respect to time of a distance, a change with respect to time of an area, a change with respect to time of a volume, or the like is observed, and a measurement value is calculated based on a result of the observation. The measurement value may be, for example, an expansion/contraction rate, a discharge amount, or the like.

In the illustrated configuration, the probe 20 has a transducer array including a plurality of transducers which are one-dimensionally arranged. An ultrasonic beam is formed by the transducer array, and the ultrasonic beam is repeatedly electronically scanned, so that a beam scanning plane 21 is repeatedly formed. As a method of electronic scanning, there are known an electronic linear scanning method, an electronic sector scanning method, and the like. As one form of the electronic linear scanning method, there is known an electron convex scanning method.

The beam scanning plane 21 is a two-dimensional data capturing region. In the figures, a first horizontal direction is an x direction, a second horizontal direction is a y direction, and a vertical direction (perpendicular direction) is a z direction. The beam scanning plane 21 is a plane parallel to a yz plane. In a phantom 22 to be described later, the x direction which is the first horizontal direction is a scanning direction, and corresponds to a time axis on which a change with respect to time of a form is expressed.

Transmission and reception will now be described in detail. During transmission, a plurality of transmission signals are supplied in parallel to each other from the transmission circuit to the transducer array. With this process, ultrasound is emitted from the transducer array to an inside of a living body (during a test, to an inside of the phantom 22 to be described later), and a transmission beam is thus formed. During reception, reflected wave from inside the living body (during the test, from inside the phantom 22) is received by the transducer array. In response to this, a plurality of reception signals are output from the transducer array toward the reception circuit in parallel to each other. In the reception circuit, a phase alignment and summing process (which is also called a delay and summing process) is applied to the plurality of reception signals, so that beam data corresponding to the reception beam are produced.

By repeatedly forming the beam scanning plane, a reception frame data array is produced. Here, one set of reception frame data is formed from a plurality of sets of beam data arranged in the electronic scanning direction, and each individual set of beam data is formed from a plurality of sets of echo data arranged in a depth direction. Based on the reception frame data array, a display frame data array is formed. Each set of display frame data corresponds to a tomographic image. With the display frame data array, a tomographic image is formed as a video image.

Alternatively, as will be described later, as the probe 20, a 3-D (three-dimensional) probe which forms a three-dimensional data capturing space may be used. The 3-D probe is a probe having a two-dimensional transducer array. Alternatively, the three-dimensional data capturing space may be formed by a mechanical scanning of a one-dimensional transducer array.

In the present embodiment, the measurement unit 19 executes the measurement based on the display frame data array. Alternatively, the measurement may be executed based on the reception frame data array. Alternatively, a configuration may be employed in which the display frame data array is transferred to an information processor such as a computer, and the measurement based on the display data may be executed at the information processor.

The testing apparatus 10 comprises a mechanism portion 12 and a controller 14. The controller 14 controls an operation of the mechanism portion 12. A synchronization signal, a control signal, and the like are supplied from the body 18 to the controller 14 as necessary. The synchronization signal is, for example, a frame synchronization signal. The ultrasonic beam is repeatedly one-dimensionally scanned based on the frame synchronization signal. Alternatively, volume data may be repeatedly two-dimensionally scanned based on a volume synchronization signal. Alternatively, a control signal may be supplied from the controller 14 to the body 18.

The mechanism portion 12 includes the phantom 22 and a scanning mechanism 24. The phantom 22 is a simulated element which acoustically simulates an inside of a living body. In the present embodiment, the phantom 22 includes a tissue-of-interest simulated element which simulates a tissue of interest, and a peripheral-tissue simulated element which simulates a peripheral tissue which is present at a periphery of the tissue of interest.

The illustrated phantom 22 is a phantom according to a first configuration of the present disclosure, and includes a uniform portion 35 and a core portion 34. The core portion 34 is a portion which simulates an amniotic fluid, a fetus (tissues other than the heart), and a heart in the mother. The uniform portion 35 is a portion corresponding to mother tissues other than these tissues. In the illustrated configuration, the heart is the tissue of interest. In a fetus of an early stage, it is difficult to clearly distinguish a substantial portion and a blood portion of the heart in the tomographic image, and the heart as a whole is set as a measurement target. The amniotic fluid and the fetus are respectively peripheral tissues. As will be described later, a size of a cross section of the portion corresponding to the heart continuously changes in the x direction.

The scanning mechanism 24 comprises a slide mechanism 26, a frame 32, and a holder 33. The slide mechanism 26 comprises a fixed portion 28 and a movable portion 30. The fixed portion 28 functions as a base, and the movable portion 30 functions as a slider. The movable portion 30 slides and moves in the x direction with respect to the fixed portion 28, and, in FIG. 1, an actuator which generates a slide force is not shown. A reciprocating movement 36 of the movable element 30 is controlled by the controller 14. A movement velocity and a movement range may be variably set by a user. Alternatively, as the scanning mechanism 24, a mechanism which can slide the movable portion 30 in the x direction and in the y direction may be provided.

The frame 32 is fixed on the movable portion 30, and includes the holder 33. The holder 33 holds the probe 20. The holder 33 detachably holds the probe 20, such that the beam scanning plane 21 formed by the probe 20 is parallel to an xy plane. When the movable portion 30 moves in the x direction, the beam scanning plane 21 moves in the x direction. That is, the beam scanning plane 21 is formed at various positions in the x direction.

Figure 2:
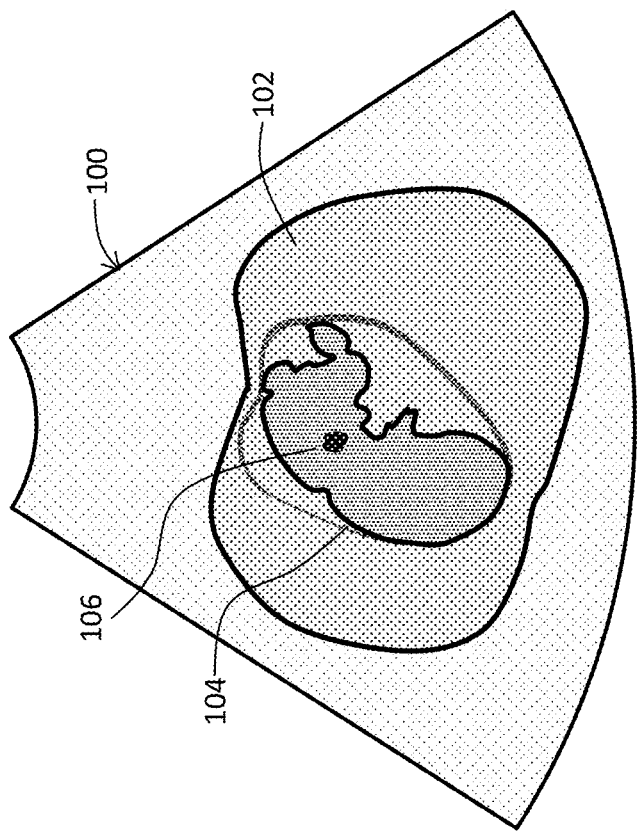
FIG. 2 is a diagram showing an example of a tomographic image of a fetus.

FIG. 2 exemplifies a tomographic image 100 acquired in the ultrasonic diagnosis of a fetus. The tomographic image 100 is a video image, and includes a fetus image 104 and an amniotic fluid image 102. The fetus image 104 includes a heart image 106. A width of the heart in the fetus of an early stage is, for example, about 2 or 3 mm. In the tomographic image 100 showing the fetus of an initial stage, it is difficult to distinguish between a cardiac muscle and a heart chamber, in the heart, and thus, the heart as a whole is set as the measurement target. In a fetus of a middle stage or a later stage, the heart chamber alone may be set as the measurement target. Alternatively, the cardiac muscle (cardiac wall) alone may be set as the measurement target. A size of the heart image changes periodically according to a pulse. For example, an area of the heart image is measured for each frame.

Figure 3:
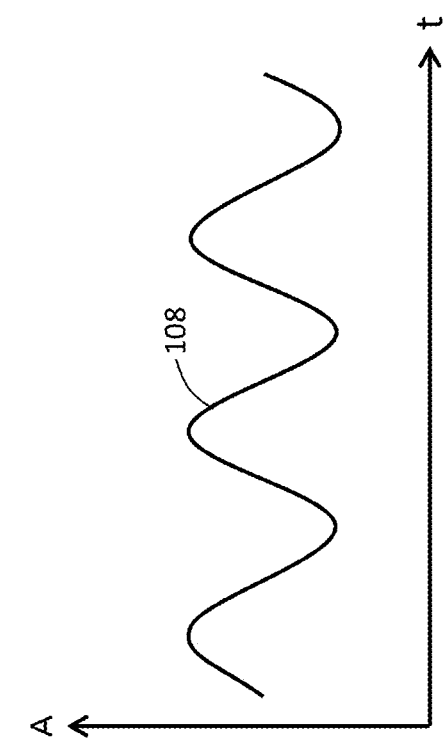
FIG. 3 is a diagram showing an example graph acquired by a measurement of a heart of a fetus.

With this process, a graph 108 as shown in FIG. 3 is produced. In FIG. 3, a horizontal axis is a time axis, and a vertical axis shows, for example, a displacement, a distance, or an area. A form of the graph 108 changes periodically with the pulse.

Figure 4:
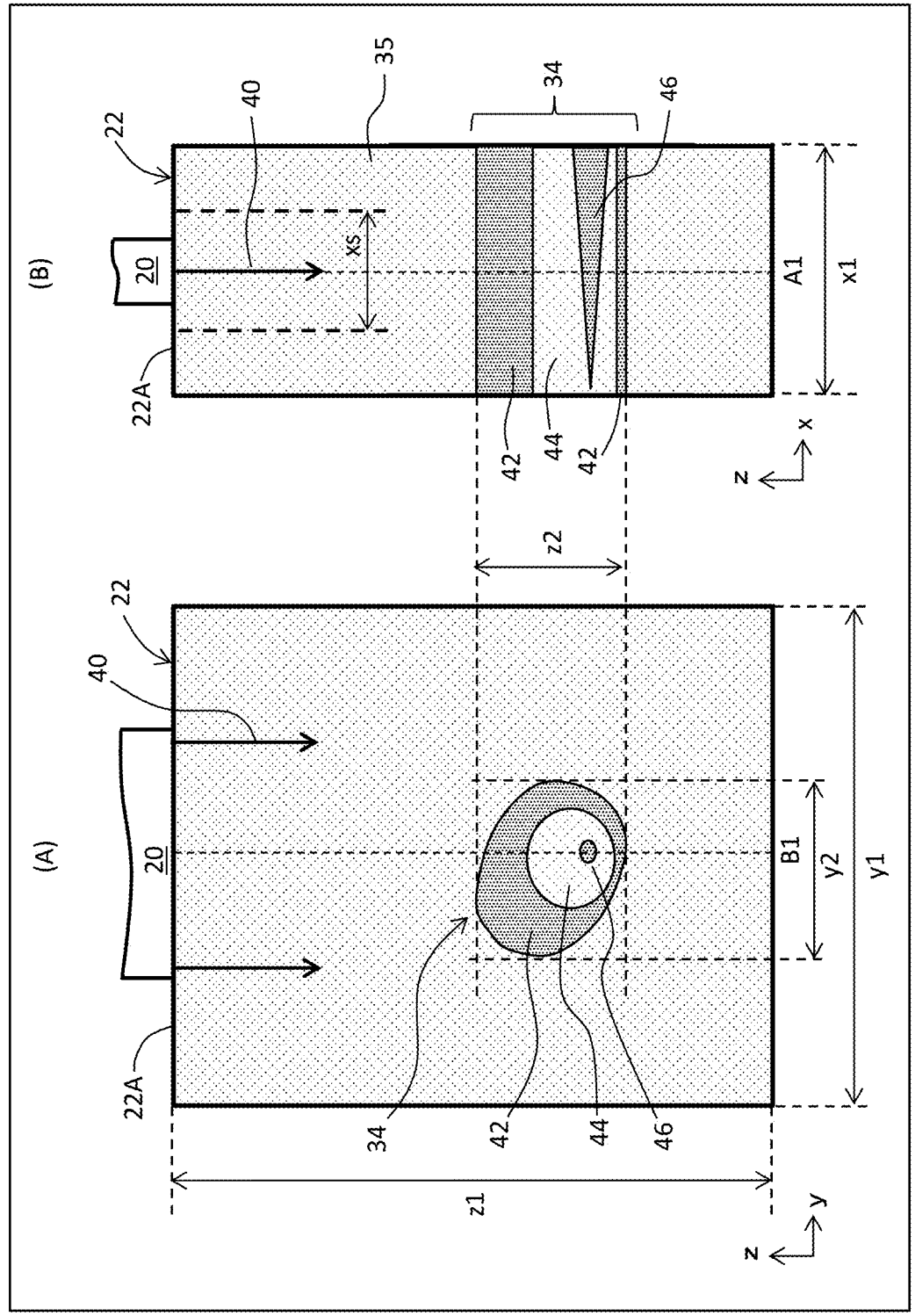
FIG. 4 is a diagram showing a phantom according to a first configuration.

FIG. 4 shows details of the phantom 22 according to the first configuration. Elements which have already been described will be assigned the same reference numerals, and repeated description thereof will be omitted. This is similarly true for each of the figures from FIG. 5 and on.

At a left side of FIG. 4, a yz cross section of the phantom 22 is shown (refer to (A) in FIG. 4), and, at a right side of FIG. 4, an xz cross section of the phantom 22 is shown (refer to (B) in FIG. 4). The illustrated yz cross section corresponds to a position A1 on the xz cross section, and the illustrated xz cross section corresponds to a position B1 on the yz cross section. As described above, the first horizontal direction is the x direction, the second horizontal direction is the y direction, and the vertical direction (perpendicular direction) is the z direction. The first horizontal direction; that is, the x direction, corresponds to a spatial axis, and also to a time axis on which a change with respect to time of the form is expressed.

As already described, the phantom 22 is formed from the uniform portion 35 and the core portion 34. The phantom 22 as a whole is a hard member. Except for respective end surfaces of the core portion 34 in the x direction, the core portion 34 is wrapped around by the uniform portion 35. That is, the core portion 34 is embedded in the phantom 22. The uniform portion 35 is a portion having a uniform acoustic impedance. The core portion 34 has a special structure, which will be described below. Portions forming the core portion 34 have an acoustic impedance which is equal to or close to the acoustic impedance of the tissue which is being simulated.

In the illustrated example configuration, the core portion 34 comprises an amniotic-fluid simulated portion (first peripheral-tissue simulated element) 42 which simulates the amniotic fluid, a fetus simulated portion (second peripheral tissue simulated element) 44 which simulates portions of the fetus other than the heart, and a heart simulated portion (tissue-of-interest simulated element) 46 which simulates the heart.

An outline of the heart simulated portion 46 on the yz cross section changes continuously in the x direction. The outline is close to an ellipse, and the size thereof gradually increases from a negative side toward the positive side in the x direction. The form of the fetus simulated portion 44 also changes continuously in the x direction. On the yz plane, an inner outline of the fetus simulated portion 44 is close to an ellipse, and continuously increases from the negative side toward the positive side in the x direction. On the yz cross section, an outer outline of the fetus simulated portion 44 is also close to an ellipse, and is uniform in the x direction. On the yz cross section, an inner outline and an outer outline of the amniotic-fluid simulated portion 42 are both close to an ellipse, and are uniform in the x direction.

A width x1 of the phantom 22 in the x direction is set, for example, in a range of 40~60 mm, a width y1 of the phantom 22 in the y direction is set, for example, in a range of 85~115 mm, and a width z1 of the phantom 22 in the z direction is set, for example, in a range of 105~135 mm. A width y2 of the core portion 34 in the y direction is set, for example, in a range of 25~45 mm, and a width z2 of the core portion 34 in the z direction is set, for example, in a range of 20~40 mm.

During a test of the ultrasound diagnostic apparatus, a transmission and reception surface of the probe 20 is brought into contact with an upper surface 22A of the phantom 22. Between the transmission and reception surface and the upper surface 22A, a coupling agent such as an acoustic jelly is introduced, in order to remove an air layer. An ultrasonic beam 40 formed by the probe 20 is repeatedly electronically scanned in the y direction. The probe 20 is mechanically scanned in the x direction by the scanning mechanism. More specifically, the probe 20 is repeatedly scanned in a reciprocating manner. The mechanical scanning is executed for a certain scanning range xs, and a size of the scanning range xs in the x direction is set, for example, in a range of 10~20 mm.

When the probe 20 is reciprocated in the x direction while the ultrasonic beam is repeatedly electronically scanned, a reception frame data array can be acquired, which is identical to or close to a reception frame data array acquired when a moving heart is observed with a stationary probe. The reception frame data array acquired from the phantom 22 or a display frame data array based on this reception frame data array is set as a calculation target, and a predetermined measurement value is calculated. A movement velocity and a movement range of the probe 20 may be designated by the user, or may be set automatically.

According to the present embodiment, it is not necessary to embed a simulated element having a changing form in the phantom 22, and it is only necessary to embed a stationary simulated element in the phantom 22. Thus, complications of the structure of the phantom 22 can be avoided. In addition, according to the embodiment, an advantage can be obtained in that unnecessary bubbles are not caused in the phantom 22.

Figure 5:
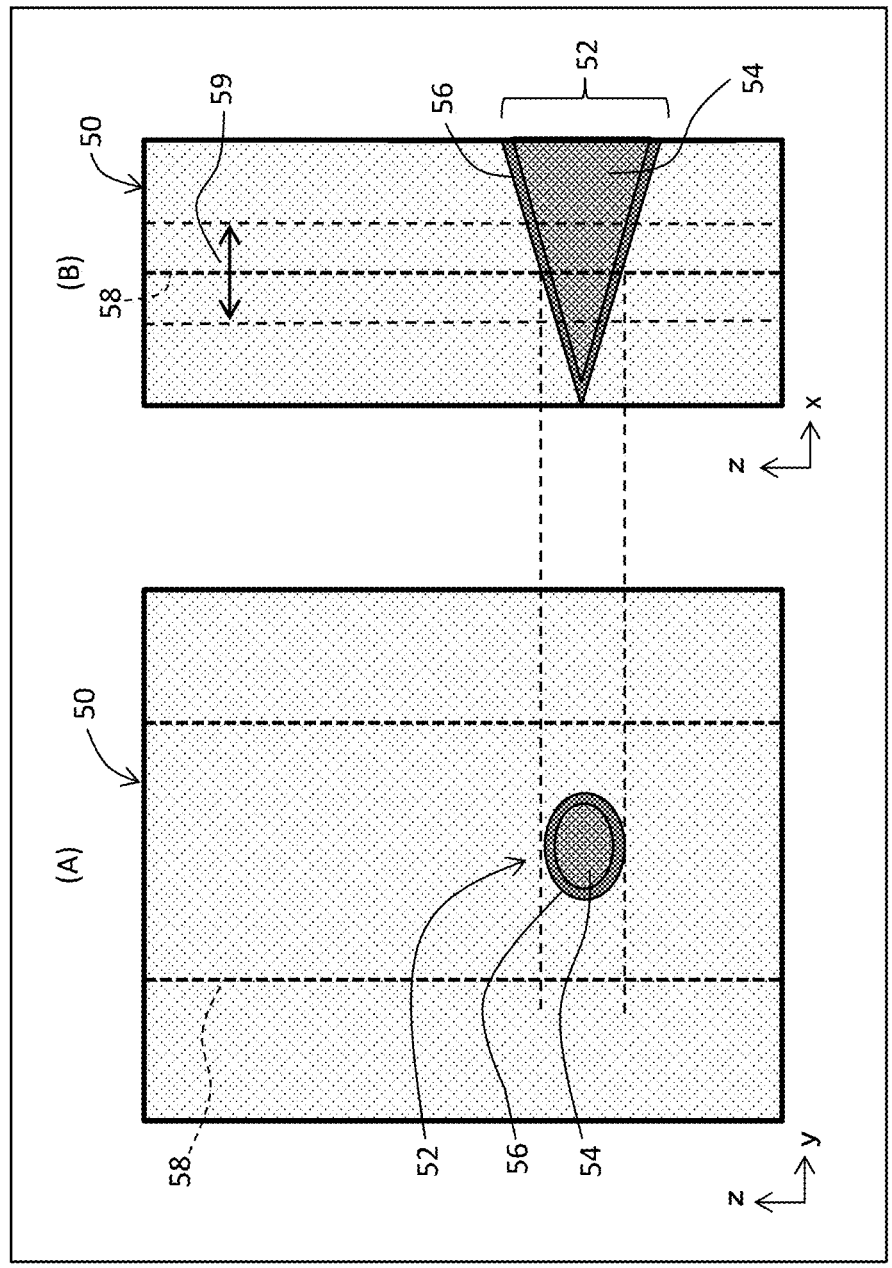
FIG. 5 is a diagram showing a phantom according to a second configuration.

FIG. 5 shows a phantom 50 according to a second configuration. In FIG. 5, (A) shows a yz cross section of the phantom 50, and (B) shows an xz cross section of the phantom 50. The phantom 50 has a core portion 52. The core portion 52 comprises an inner-cavity simulated portion (first tissue-of-interest simulated element) 54 which simulates an inner cavity of the heart, and a cardiac-wall simulated portion (second tissue-of-interest simulated element) 56 which simulates a cardiac wall at a periphery of the inner cavity. A portion which is present at a periphery of the core portion 52 is a portion which simulates a tissue which is present at the periphery of the heart and a tissue which is present at the periphery of the fetus (peripheral-tissue simulated element).

The inner-cavity simulated portion 54 has an elliptical form in the yz cross section, and has a three-dimensional form of a circular conical shape. The cardiac-wall simulated portion 56 has an elliptical ring-shape form in the yz cross section, and has a three-dimensional form of a hollow cone. A beam scanning plane 58 is continuously repeatedly scanned in a reciprocating manner over a scanning range 59 in the x direction. With this process, a reception frame data array can be acquired, which is close to a reception frame data array which is acquired when a moving heart is observed with an ultrasonic probe in a stationary state.

One or both of the inner-cavity simulated portion 54 and the cardiac-wall simulated portion 56 is/are set as the observation target. For example, a change with respect to time of an area of the inner cavity may be measured, or a movement with respect to time of a particular location in the cardiac-wall simulated portion 56 may be measured. The phantom 50 shown in FIG. 5 simulates the heart in the fetus of the middle stage or the later stage.

Figure 6:
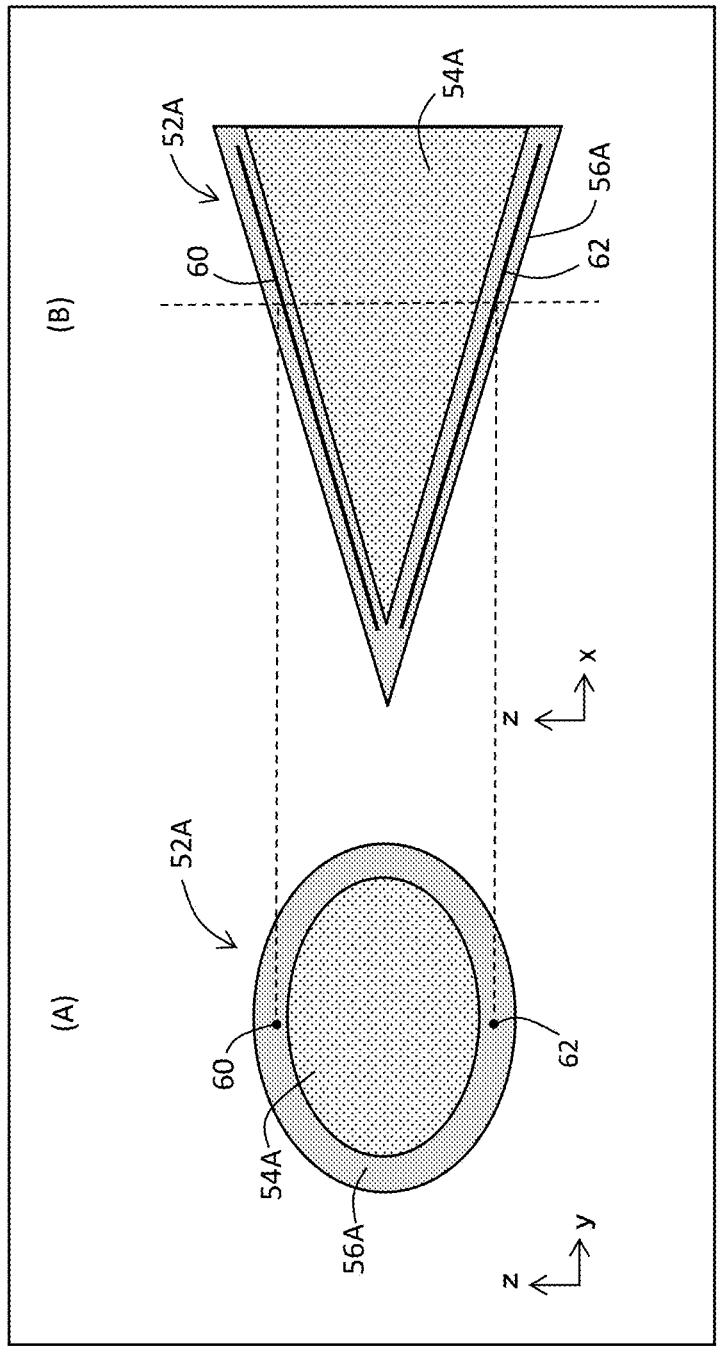
FIG. 6 is a diagram showing an alternative form of the second configuration.

FIG. 6 shows an alternative form of the second configuration. In the alternative form, basically, a structure similar to that of the second configuration is employed. FIG. 6 only shows a core portion 52A of the phantom. The core portion 52A comprises a heart-chamber simulated portion 54A and a cardiac-wall simulated portion 56A. Two line-form elements 60 and 62 are embedded in the cardiac-wall simulated portion 56A. Each of the line-form elements 60 and 62 is formed from a metal line, which functions as a strong reflective element. The line-form elements 60 and 62 are placed along a direction of extension of the cardiac-wall simulated portion 56A, and are inclined with respect to the x direction.

On cross sections crossing various positions in the x direction, the two line-form elements 60 and 62 appear as two dots. On the tomographic image which is the video image, the positions of the dots change periodically. Each individual dot in each frame is set as a tracking target. For the tracking of each dot, pattern matching between frames, or the like may be executed. Alternatively, one of the two dots may be set as the tracking target. Alternatively, three or more line-form elements may be placed. Alternatively, two line-form elements may be placed at a boundary between the heart-chamber simulated portion and a cardiac-muscle simulated portion.

Figure 7:
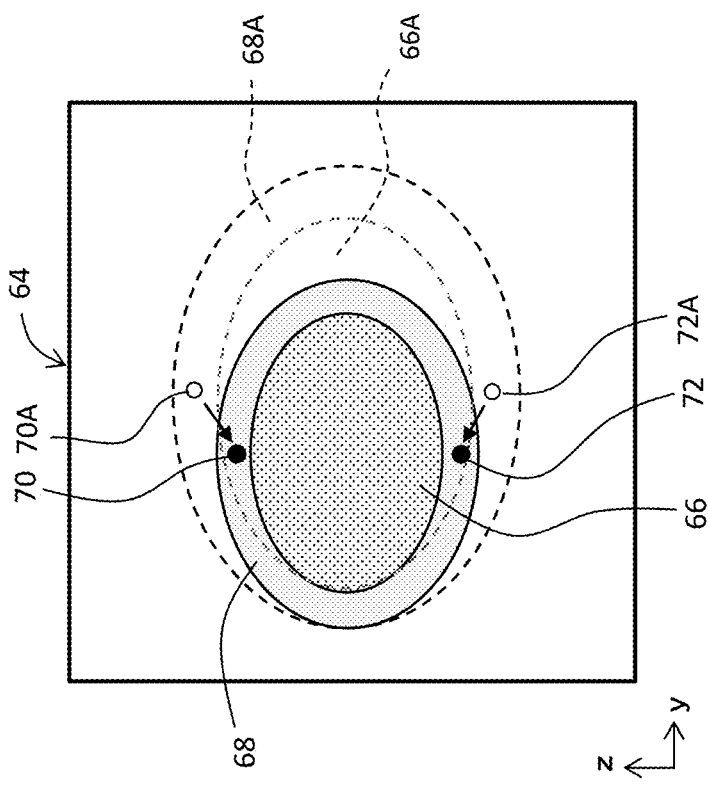
FIG. 7 is a diagram showing a phantom according to a third configuration.

FIG. 7 shows a phantom 64 of a third configuration. The phantom 64 has an outer form similar to that of the phantom of the first configuration, and a core portion is embedded therein. The core portion comprises a heart-chamber simulated portion and a cardiac-wall simulated portion 68, and two line-form elements are embedded in the cardiac-wall simulated portions, similar to the alternative form described above.

On a certain yz cross section, a cross section 66 of the heart-chamber simulated portion appears, and a cross section of the cardiac-wall simulated portion 68 appears. Also, cross sections 70 and 72 of the two line-form elements appear. On another yz cross section, a cross section 66A of the heart-chamber simulated portion appears, and a cross section of a cardiac-wall simulated portion 68A appears. In addition, cross sections 70A and 72A of the two line-form elements appear. As is represented as a difference between two yz cross sections, in the third configuration, a center of gravity of the heart is displaced. With the displacement of the center of gravity, the positions of the cross sections of the two line-form elements are also displaced.

Figure 8:
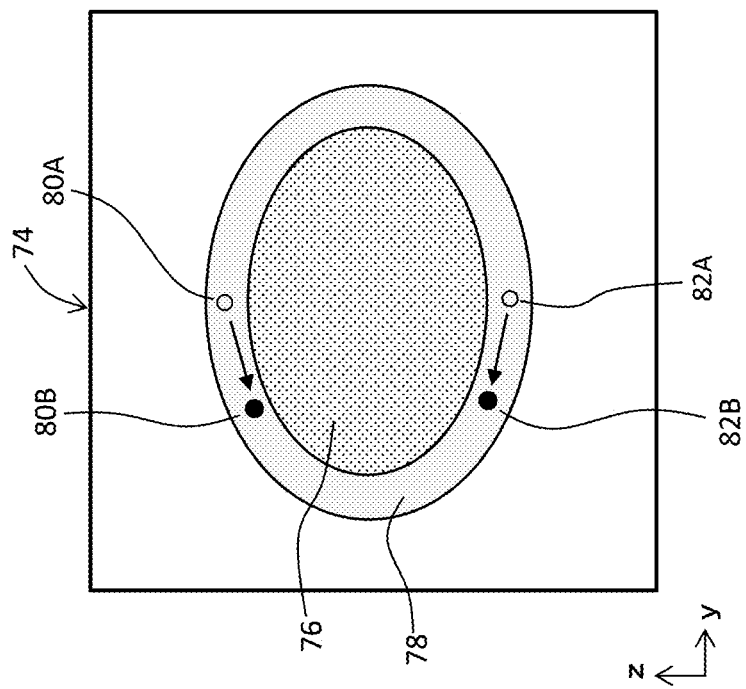
FIG. 8 is a diagram showing a phantom according to a fourth configuration.

FIG. 8 shows a phantom 74 of a fourth configuration. The phantom 74 has an outer form similar to that of the phantom of the first configuration, and a core portion is embedded therein. The core portion comprises a heart-chamber simulated portion and a cardiac-wall simulated portion, and two line-form elements are embedded in the cardiac-wall simulated portion, similar to the alternative form described above.

On each yz cross section, a cross section 76 of the heart-chamber simulated portion appears, and a cross section of a cardiac-wall simulated portion 78 appears. The forms of the cross sections are identical with each other except for positions of the two line-form elements. The two line-form elements are inclined with respect to the x direction. On a certain yz cross section, cross sections 80A and 82A of the two line-form elements appear near a center in the y direction. On another yz cross section, cross sections 80B and 82B of the two line-form elements appear at positions deviated in the y direction.

Figure 9:
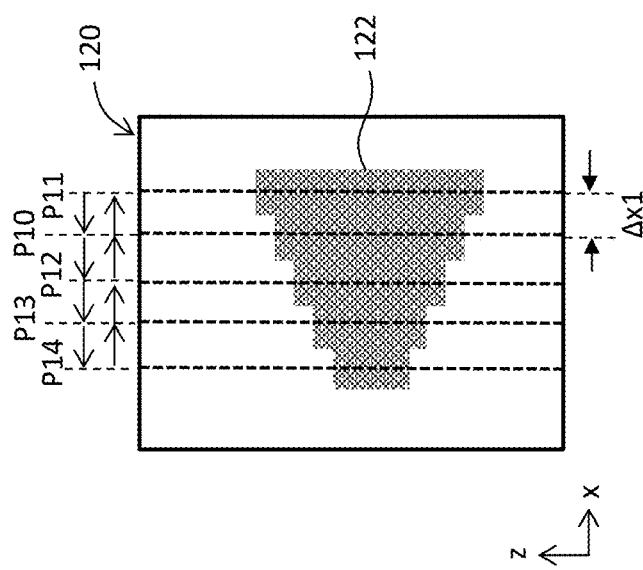
FIG. 9 is a diagram showing a phantom according to a fifth configuration.

FIG. 9 shows a phantom 120 of a fifth configuration. The phantom 120 has a cube shape as a whole, and a core portion 122 is embedded therein. The core portion 122 comprises a plurality of circular discs which have sizes changed stepwise along the x direction and which are layered. The plurality of circular discs are arranged with a pitch of $\Delta x1$. A width of each disc in the x direction is $\Delta x1$. In FIG. 9, P11~P14 show probe stopping positions in the scanning direction (x direction). The probe is stepwise moved in a non-continuous manner; that is, is repeatedly moved and stopped. For example, at a position P1, an electronic scanning is executed once, and then, the probe is moved to a position P2, where an electronic scanning is executed once. Such operations are repeated in an outward path and in a return path. The movement of the probe is executed, for example, in a blank period between frames.

Figure 10:
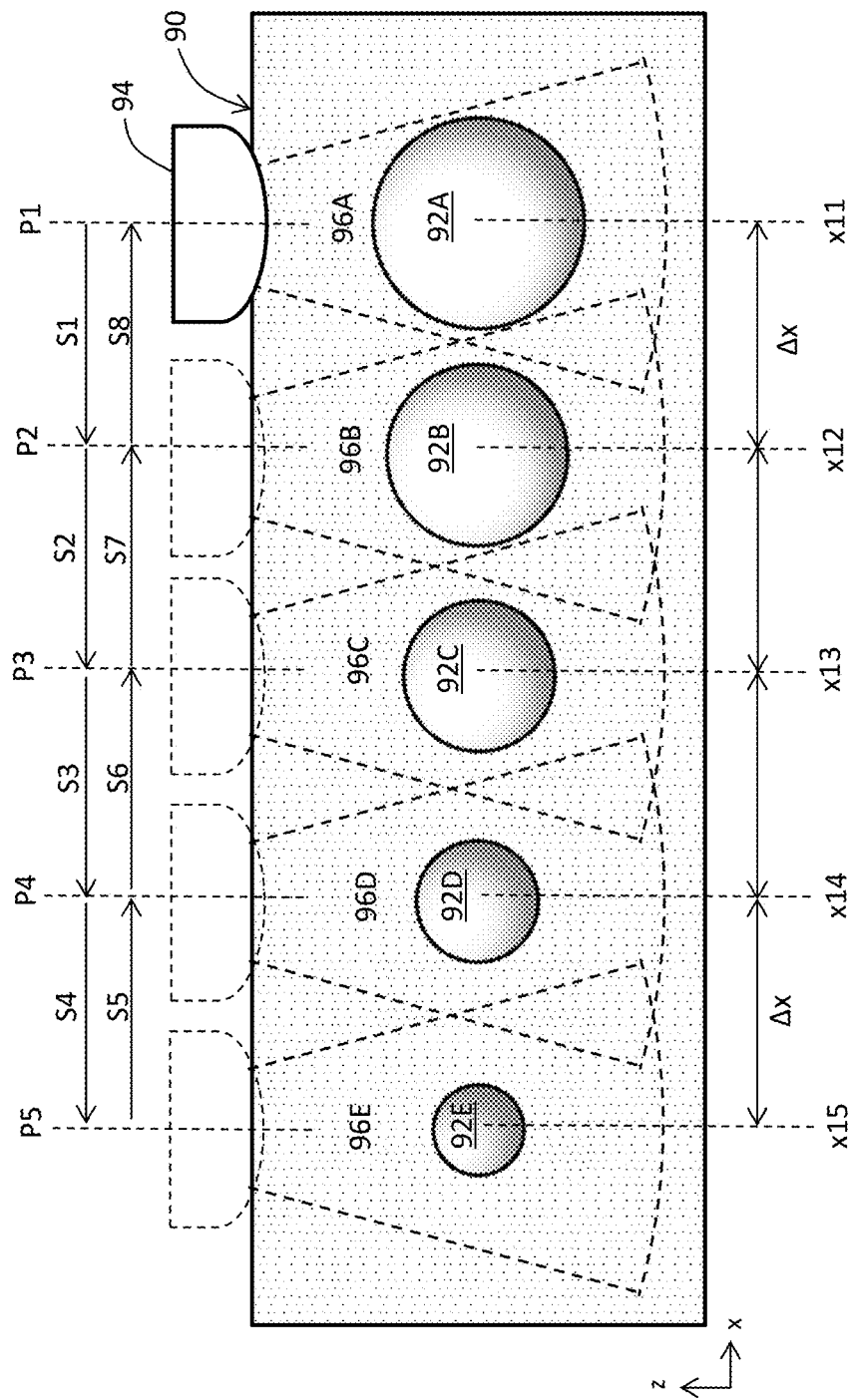
FIG. 10 is a diagram showing a phantom according to a sixth configuration.

FIG. 10 shows a phantom 90 of a sixth configuration. The phantom 90 has a cube shape as a whole, and a plurality of simulated parts 92A~92E are embedded therein as a tissue-of-interest simulated element. The tissue of interest is, for example, a left ventricle in the heart. The plurality of simulated parts 92A~92E have a plurality of three-dimensional forms corresponding to a plurality of time phases. In other words, each of the simulated parts 92A~92E artificially simulates the three-dimensional form of the left ventricle at each time phase. The plurality of simulated parts 92A~92E are provided at a plurality of positions x11~x15, which are arranged in the x direction with a constant pitch, $\Delta x$. A probe 94 is a 3-D probe.

In FIG. 10, positions P1~P5 show stopping positions of the 3-D probe 94 in the mechanical scanning. At each of the positions P1~P5, a two-dimensional scanning of the ultrasonic beam is executed. With this process, three-dimensional data capturing spaces 96A~96E are formed at the positions P1~P5, and volume data are thus acquired. A plurality of sets of the volume data correspond to a plurality of time phases, and may be processed, to construct a three-dimensional video image of the tissue of interest. A step movement of the 3-D probe 94 is shown by S1~S8. The 3-D probe 94 is repeatedly moved in a reciprocating manner in the mechanical scanning direction; that is, the x direction. For each two-dimensional scanning of the ultrasonic beam, at a subsequent blank period, the position of the probe is switched.

According to the sixth configuration, a plurality of sets of volume data corresponding to a plurality of time phases can be acquired using the tissue-of-interest simulated element. Because the tissue-of-interest simulated element is a stationary element, bubbles are not caused therein. In the sixth configuration, desirably, an arrangement of the plurality of simulated parts is determined in consideration of an arrangement of the plurality of three-dimensional data capturing spaces. Alternatively, desirably, a size of each individual three-dimensional data capturing space is determined according to the arrangement of the plurality of simulated parts. Alternatively, the pitch $\Delta x$ described above may be set to differ in the x direction.

Figure 11:
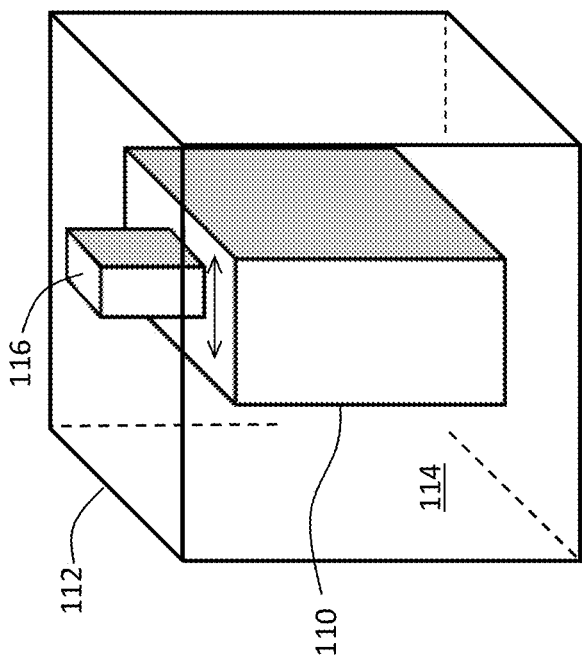
FIG. 11 is a diagram for explaining use of a water tank.

FIG. 11 shows a phantom 110 placed in a water tank 112. Water 114 is housed in the water tank 112. Even if there is a gap between a transmission and reception surface of a probe 116 and an upper surface of the phantom 110, because the water 114 is present in the gap, ultrasound propagation in the gap can be secured.

Figure 12:
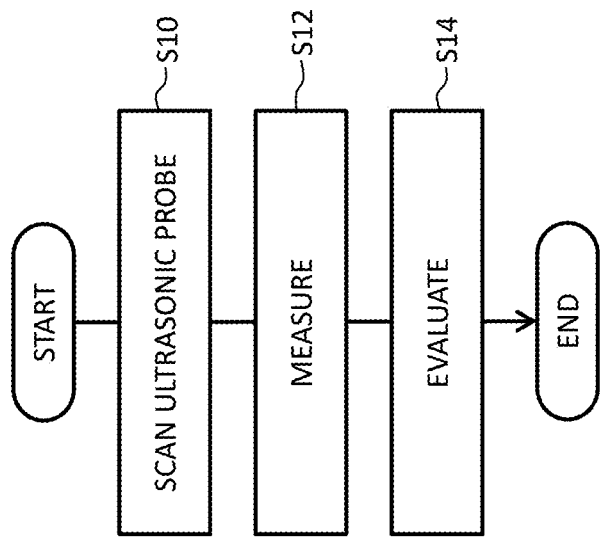
FIG. 12 is a flowchart showing a testing method according to an embodiment of the present disclosure.

FIG. 12 shows a testing method according to the present embodiment as a flowchart. In S10, the probe is mechanically scanned in a reciprocating manner with respect to the phantom. With this process, a frame data array or a volume data array is acquired. In S12, a measurement based on the frame data array or based on the volume data array is executed, to calculate a measurement value. In S14, the measurement value is evaluated, to confirm that the measurement function of the ultrasound diagnostic apparatus is appropriate. The evaluation in S14 may be executed by an inspector.

In the above-described configurations, the phantom is fixed and the probe is mechanically scanned. Alternatively, the probe may be fixed, and the phantom may be mechanically scanned. The constituent elements of the phantom may be formed by a solid, a liquid, a gel, or the like. By forming the phantom as a whole from a hard member, handling of the phantom can be facilitated.

Desirably, the mechanical scanning is executed on a straight line path, but alternatively, the mechanical scanning may be executed on a ring-form path. In this case, a direction and an orientation of the probe are adjusted such that the beam scanning plane is orthogonal to the ring-form path. In the embodiment, a change with respect to time over a half period (from a diastolic phase to a systolic phase, or from the systolic phase to the diastolic phase) is expressed as a change of a form, but alternatively, a change with respect to time over one period or over a plurality of periods may be expressed as a sequence of changes of the form. Alternatively, a plurality of core portions may be embedded in one phantom. In this case, the plurality of core portions may be arranged with a certain interval therebetween in a direction orthogonal to the direction of mechanical scanning. A core portion to be used may then be selected by selecting a position of the probe in the y direction.

The invention claimed is:

1. A testing apparatus comprising:
a phantom that includes a uniform portion and a core portion wrapped around by the uniform portion, the core portion comprising a first peripheral-tissue simulated element, a second peripheral-tissue simulated element and a simulated element of a tissue-of-interest, the simulated element of the tissue-of-interest simulating a change with respect to time of the tissue-of-interest as a change of a form of the simulated element of the tissue-of-interest in a scanning direction; and
a scanning mechanism that moves an ultrasonic probe relatively with respect to the phantom in the scanning direction,
wherein the simulated element of the tissue-of interest includes a plurality of forms corresponding to a plurality of time phases in a periodic movement of the tissue-of-interest, the plurality of forms being arranged continuously in the scanning direction,
wherein the first peripheral-tissue simulated element simulates an amniotic fluid and is present at a periphery of the second peripheral-tissue simulated element,
wherein the second peripheral-tissue simulated element simulates portions of a fetus other than a heart of the fetus and is present at a periphery of the simulated element of the tissue-of-interest, and
wherein the simulated element of the tissue-of-interest simulates the heart of the fetus.

* * * * *